(12) United States Patent
Matthews et al.

(10) Patent No.: US 11,060,057 B2
(45) Date of Patent: Jul. 13, 2021

(54) PRESATURATION OF SUPERCRITICAL $CO_2$ WITH WATER FOR DECELLULARIZATION OF MATRICES

(71) Applicant: University of South Carolina, Columbia, SC (US)

(72) Inventors: Michael Matthews, Columbia, SC (US); Dominic M. Casali, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/644,241

(22) Filed: Mar. 11, 2015

(65) Prior Publication Data

US 2015/0315540 A1    Nov. 5, 2015

Related U.S. Application Data

(60) Provisional application No. 61/967,155, filed on Mar. 11, 2014.

(51) Int. Cl.
*C12N 5/00* (2006.01)
*A61L 27/36* (2006.01)

(52) U.S. Cl.
CPC ........ *C12N 5/0081* (2013.01); *A61L 27/3691* (2013.01); *A61L 2430/40* (2013.01); *C12N 2509/00* (2013.01); *C12N 2521/00* (2013.01)

(58) Field of Classification Search
CPC  A01N 25/10; A61K 35/32; A61F 2/28; A61F 2250/006; A61F 2310/00359
USPC ........................................................ 435/378
See application file for complete search history.

(56) References Cited

U.S. PATENT DOCUMENTS

| | | | |
|---|---|---|---|
| 5,135,766 A * | 8/1992 | Hermsen ................. | A23F 5/206 426/427 |
| 2007/0009606 A1* | 1/2007 | Serdy ....................... | A61F 2/28 424/497 |
| 2014/0205674 A1* | 7/2014 | Wei ........................ | A61K 35/28 424/549 |

OTHER PUBLICATIONS

Sawada et al. "Cell removal with supercritical carbon dioxide for a cellular artificial tissue" Journal of Chemical Technology and Biotechnology 83:943-949 (2008).*
Gumerov et al. "Solubility of Water in Supercritical Carbon Dioxide" High Temperature, vol. 40, No. 2, 2002 pp. 231-234.*
The Need is Real: Data [http://www.organdonor.gov/about/data.html].
Artificial Organ History: A Selective Timeline [http://echo.gmu.edu/bionics/exhibits.htm].
Deeken CR, White AK, Bachman SL, Ramshaw BJ, Cleveland DS, Loy TS, Grant SA: Method of preparing a decellularized porcine tendon using tributyl phosphate. J Biomed Mater Res Part B 2011, 96B (2):199-206.
Remlinger NT, Czajka CA, Juhas ME, Vorp DA, Stolz DB, Badylak SF, Gilbert S, Gilbert TW: Hydrated xenogeneic decellularized tracheal matrix as a scaffold for tracheal reconstruction. Biomaterials 2010, 31(13):3520-3526.
Crapo PM, Gilbert TW, Badylak SF: An overview of tissue and whole organ decellularization processes. Biomaterials 2011, 32(12):3233-3243.
Keane TJ, Londono R, Turner NJ, Badylak SF: Consequences of ineffective decellularization of biologic scaffolds on the host response. Biomaterials 2012, 33(6):1771-1781.
Ferrentino G, Spilimbergo S: High pressure carbon dioxide pasteurization of solid foods: Current knowledge and future outlooks. Trends in Food Science & Technology 2011, 22(8):427-441.
Ferrentino G, Belscak-Cvitanovic A, Komes D, Spilimbergo S: Quality Attributes of Fresh-Cut Coconut after Supercritical Carbon Dioxide Pasteurization. Journal of Chemistry 2013.
Ferrentino G, Balzan S, Spilimbergo S: On-line color monitoring of solid foods during supercritical CO2 pasteurization. Journal of Food Engineering 2012, 110(1):80-85.
Wagner ME, French J, Rizvi SSH: Supercritical fluid extraction of oil from potato chips: Two scale comparison and mathematical modeling. Journal of Food Engineering 2013, 118(1):100-107.
Harde SM, Kagliwal LD, Singhal RS, Patravale VB: Supercritical fluid extraction of forskolin from Coleus forskohlii roots. Journal of Food Engineering 2013, 117(4):443-449.
Abstract of An YH, Alvi FI, Kang Q, Laberge M, Drews MJ, Zhang J, Matthews MA, Arciola CR: Effects of sterilization on implant mechanical property and biocompatibility. Int J Artif Organs 2005, 28(11):1126-1137.
Hemmer JD, Drews MJ, Laberge M, Matthews MA: Sterilization of bacterial spores by using supercritical carbon dioxide and hydrogen peroxide. J Biomed Mater Res Part B 2007, 80B (2):511-518.
Jimenez A, Thompson GL, Matthews MA, Davis TA, Crocker K, Lyons JS, Trapotsis A: Compatibility of medical-grade polymers with dense CO2. J Supercrit Fluids 2007, 42(3):366-372.
Jimenez A, Zhang J, Matthews MA: Evaluation of CO2-Based Cold Sterilization of a Model Hydrogel. Biotechnol Bioeng 2008, 101(6):1344-1352.
Tarafa PJ, Jimenez A, Zhang JA, Matthews MA: Compressed carbon dioxide (CO2) for decontamination of biomaterials and tissue scaffolds. J Supercrit Fluids 2010, 53(1-3):192-199.

(Continued)

*Primary Examiner* — Blaine Lankford
(74) *Attorney, Agent, or Firm* — Dority & Manning, PA (57) ABSTRACT

Decellularization methods for tissue are provided. The method can include: exposing a tissue to a water-saturated, supercritical $CO_2$. The method can further comprise, prior to exposing the tissue to the water-saturated, supercritical $CO_2$, saturating a stream of supercritical $CO_2$. The tissue can be exposed to the water-saturated, supercritical $CO_2$ at a treatment temperature of about 35° C. to about 40° C. (e.g., about 37° C.). In one embodiment, the water-saturated, supercritical $CO_2$ is completely saturated with water at the treatment temperature. The tissue can be exposed to the water-saturated, supercritical $CO_2$ at a constant flow rate, such as less than 3 mL/min (e.g., about 0.5 mL/min to about 2.5 mL/min).

13 Claims, 9 Drawing Sheets

(56) References Cited

OTHER PUBLICATIONS

Zhang J, Burrows S, Gleason C, Matthews MA, Drews MJ, Laberge M, An YHH: Sterilizing Bacillus pumilus spores using supercritical carbon dioxide. J Microbiol Methods 2006, 66(3):479-485.

Zhang J, Dalal N, Gleason C, Matthews MA, Waller LN, Fox KF, Fox A, Drews MJ, Laberge M, An YH: On the mechanisms of deactivation of Bacillus atrophaeus spores using supercritical carbon dioxide. J Supercrit Fluids 2006, 38(2):268-273.

Zhang J, Dalal N, Matthews MA, Waller LN, Saunders C, Fox KF, Fox A: Supercritical carbon dioxide and hydrogen peroxide spore structures associated with high killing rate cause mild changes in of Bacillus anthracis. J Microbiol Methods 2007, 70(3):442-451.

Zhang J, Davis TA, Matthews MA, Drews MJ, Laberge M, An YHH: Sterilization using high-pressure carbon dioxide. J Supercrit Fluids 2006, 38(3):354-372.
Gasperi F, Aprea E, Biasioli F, Carlin S, Endrizzi I, Pirretti G, Spilimbergo S: Effects of supercritical CO2 and N2O pasteurisation on the quality of fresh apple juice. Food Chemistry 2009, 115(1):129-136.
Spilimbergo S, Ciola L: Supercritical CO2 and N2O pasteurisation of peach and kiwi juice. International Journal of Food Science and Technology 2010, 45(8):1619-1625.
Akhyari P, Aubin H, Gwanmesia P, Barth M, Hoffmann S, Huelsmann J, Preuss K, Lichtenberg A: The Quest for an Optimized Protocol for Whole-Heart Decellularization: A Comparison of Three Popular and a Novel Decellularization Technique and Their Diverse Effects on Crucial Extracellular Matrix Qualities. Tissue Eng Part C-Methods 2011, 17(9):915-926.
Baptista PM, Siddiqui MM, Lozier G, Rodriguez SR, Atala A, Soker S: The Use of Whole Organ Decellularization for the Generation of a Vascularized Liver Organoid. Hepatology 2011, 53(2):604-617.
Sano MB, Neal RE, Garcia PA, Gerber D, Robertson J, Davalos RV: Towards the creation of decellularized organ constructs using irreversible electroporation and active mechanical perfusion. Biomed Eng Online 2010, 9.
Petersen TH, Calle EA, Zhao LP, Lee EJ, Gui LQ, Raredon MB, Gavrilov K, Yi T, Zhuang ZW, Breuer C et al: Tissue-Engineered Lungs for in Vivo Implantation. Science 2010, 329(5991):538-541.
Price AP, England KA, Matson AM, Blazar BR, Panoskaltsis-Mortari A: Development of a Decellularized Lung Bioreactor System for Bioengineering the Lung: The Matrix Reloaded. Tissue Eng Part A 2010, 16(8):2581-2591.
Prasertsung I, Kanokpanont S, Bunaprasert T, Thanakit V, Damrongsakkul S: Development of acellular dermis from porcine skin using periodic pressurized technique. J Biomed Mater Res Part B 2008, 85B(1):210-219.
Hudson TW, Liu SY, Schmidt CE: Engineering an improved acellular nerve graft via optimized chemical processing. Tissue Eng 2004, 10(9-10):1346-1358.
Bolland F, Korossis S, Wilshaw SP, Ingham E, Fisher J, Kearney JN, Southgate J: Development and characterisation of a full-thickness acellular porcine bladder matrix for tissue engineering. Biomaterials 2007, 28(6):1061-1070.
Dequach JA, Yuan SH, Goldstein LSB, Christman KL: Decellularized Porcine Brain Matrix for Cell Culture and Tissue Engineering Scaffolds. Tissue Eng Part A 2011, 17(21-22):2583-2592.
Choi JS, Kim BS, Kim JY, Kim JD, Choi YC, Yang H-J, Park K, Lee HY, Cho YW: Decellularized extracellular matrix derived from human adipose tissue as a potential scaffold for allograft tissue engineering. Journal of Biomedical Materials Research Part A 2011, 97A(3):292-299.
Sawada K, Terada D, Yamaoka T, Kitamura S, Fujisato T: Cell removal with supercritical carbon dioxide for acellular artificial tissue. J Chem Technol Biotechnol 2008, 83(6):943-949.
Phillips M, Maor E, Rubinsky B: Nonthermal Irreversible Electroporation for Tissue Decellularization. J Biomech Eng-Trans ASME 2010, 132(9).
Montoya CV, Mcfetridge PS: Preparation of Ex Vivo-Based Biomaterials Using Convective Flow Decellularization. Tissue Eng Part C-Methods 2009, 15(2):191-200.
Badylak SF, Taylor D, Uygun K: Whole-Organ Tissue Engineering: Decellularization and Recellularization of Three-Dimensional Matrix Scaffolds. Annual Review of Biomedical Engineering 2011, 13(1):27-53.
Qiu QQ, Leamy P, Brittingham J, Pomerleau J, Kabaria N, Connor J: Inactivation of Bacterial Spores and Viruses in Biological Material Using Supercritical Carbon Dioxide With Sterilant. J Biomed Mater Res Part B 2009, 91B(2):572-578.
Zhang Q, Raoof M, Chen Y, Sumi Y, Sursal T, Junger W, Brohi K, Itagaki K, Hauser CJ: Circulating mitochondrial DAMPs cause inflammatory responses to injury. Nature 2010, 464(7285):104-U115.
Xu H, Wan H, Sandor M, Qi SJ, Ervin F, Harper JR, Silverman RP, Mcquillan DJ: Host Response to Human Acellular Dermal Matrix Transplantation in a Primate Model of Abdominal Wall Repair. Tissue Engineering Part A 2008, 14(12):2009-2019.
Burch PT, Kaza AK, Lambert LM, Holubkov R, Shaddy RE, Hawkins JA: Clinical Performance of Decellularized Cryopreserved Valved Allografts Compared With Standard Allografts in the Right Ventricular Outflow Tract. Annals of Thoracic Surgery 2010, 90(4):1301-1305.
Abstract of Rice RD, Ayubi FS, Shaub ZJ, Parker DM, Armstrong PJ, Tsai JW: Comparison of Surgisis(A (R)), AlloDerm(A (R)), and Vicryl Woven Mesh(A (R)) Grafts for Abdominal Wall Defect Repair in an Animal Model. Aesthetic Plastic Surgery 2010, 34(3):290-296.
Guo X, Lanir Y, Kassab GS: Effect of osmolarity on the zero-stress state and mechanical properties of aorta. American Journal of Physiology—Heart and Circulatory Physiology 2007, 293(4):H2328-H2334.
Khosravi-Darani K: Research Activities on Supercritical Fluid Science in Food Biotechnology. Critical Reviews in Food Science and Nutrition 2010, 50(6):479-488.
Sabirzyanov AN, Il'In AP, Akhunov AR, Gumerov FM: Solubility of water in Supercritical carbon dioxide. High Temperature 2002, 40(2):203-206.
Mol A, Rutten MC, Driessen NJ, Bouten CV, Zund G, Baaijens FP, Hoerstrup SP: Tissue engineering of living, functional human heart valves suitable for aortic valve replacement. Circulation 2005, 112(17):U777-U778.

* cited by examiner

PRESATURATION OF SUPERCRITICAL $CO_2$ WITH WATER FOR DECELLULARIZATION OF MATRICES

PRIORITY INFORMATION

The present application claims priority to U.S. Provisional Patent Application Ser. No. 61/967,155 titled "Presaturation of Supercritical $CO_2$ with Water for Decellularization of Matrices" of Matthews, et al. filed on Mar. 11, 2014; the disclosure of which is incorporated by reference herein.

BACKGROUND

This year in the United States, nearly 7,000 people will die while on the waiting list for an organ transplant, according to the US government organ donation page, organdonor.gov. Additionally, the size of the waiting list has increased considerably in the past 25 years, while the number of registered donors has stagnated. As a result, the number of deaths that occur while people are on the waiting list will increase in the future. These statistics suggest that merely relying on human organ donors will not be sufficient for providing the required number of organ donations to save the lives of people requiring an organ transplant. One potential way to address this problem is through the use of artificial organs.

Though the concept of artificial organs has existed for over a century, widespread clinical use of artificial organs does not exist. One exciting and relatively novel approach to creating artificial organs is the field of tissue engineering. Tissue engineering involves seeding cells onto a biocompatible three-dimensional construct called a tissue scaffold and then implanting the tissue scaffold into the body. Once inside the body, the cells grow and divide, populating about the scaffold and eventually forming a new tissue or organ that replaces the damaged one.

There are a number of challenges that have prevented the use of tissue scaffolds in this fashion. The first challenge is the source of the scaffold. Two main approaches are possible: producing scaffolds from synthetic biomaterials, and using natural organs or tissues. Using natural materials is presumed to be advantageous because natural materials should significantly decrease the possibility of bodily rejection and adverse immune response often observed with synthetic biomaterials.

Natural organs or tissues contain foreign cellular material, which must be removed prior to seeding the scaffold, which is referred to as "decellularization." The objective of any decellularization method is twofold: (1) the removal of all cellular material, and (2) the preservation of the physical and chemical properties of the extracellular matrix (ECM). Decellularization is currently accomplished by contacting xenographic tissue with a combination of chemical detergents and biological agents. The main challenge regarding decellularization is finding a balance between preserving the properties of the matrix while effectively removing undesired components. If treatment is too harsh, the ECM will be damaged, compromising mechanical integrity; if the treatment is too gentle, not all foreign cells will be removed, leading to immune response. Either of these outcomes will prevent the tissue from growing and functioning properly; therefore, the efficacy of a given decellularization technique must be determined by evaluating both criteria. Currently, there are no accepted quantitative standards (such as mechanical strength or extent of DNA removal) against which to certify the viability of the decellularized material. However, future standards will certainly include characteristics like water content, removal of nuclear material, and mechanical strength.

Decellularization is currently an extremely open and diverse biomedical research field. There are many decellularization methods; those employ many different decellularization agents as well as many different techniques for applying them. Furthermore, decellularization has been attempted on to a variety of different tissues and organs, including heart, liver, lung, skin, nerve, bladder, brain, and others. Tissues have several different mammalian sources, primarily porcine and murine, but also bovine, ferret, and others. Because of these many variables and the lack of universal decellularization standards (for both removal of cellular material and ECM preservation), it can be difficult to compare decellularization results or techniques. It is also challenging at this time to predict which decellularized materials have the potential to be mass-produced and industrially utilized for human implantation.

Tissue decellularization has been investigated extensively in the past decade, and a myriad of decellularization protocols have been established. They can be classified into three main categories: chemical, biological, and physical treatments. Often, decellularization researchers will combine multiple agents together to create a unique protocol.

The most common form of chemical treatments involves chemical detergents. These can be ionic, nonionic, or zwitterionic. A common ionic detergent is sodium dodecyl sulfate (SDS), which was used to decellularize human adipose tissue and to treat porcine brain tissue. The most commonly used nonionic detergent is a surfactant solution known by its trade name, Triton X-100. This surfactant is used ubiquitously. For example, Triton X-100 was used for treatment of animal livers. It is sometimes combined with SDS or other ionic solutions to create more robust treatment methods. Zwitterionic detergents, such as tributyl phosphate and CHAPS, are often effective in treating tissues with small thicknesses. However, detergents can eventually cause degradation of the ECM under prolonged treatments, so excessive use of them is discouraged.

Biological agents can also be effective in destroying and removing cellular material from tissues. In particular, certain enzymes can break the bonds in large organic molecules, such as peptides and nucleotides. For example, others have used DNase and RNase in conjunction with SDS to achieve more complete decellularization than with SDS alone in their adipose decellularization. Chelating agents, such as ethylenediaminetetraacetic acid (EDTA), can also break bonds between cells and the ECM.

Finally, physical treatment can be used to unattach cells from the ECM. Agitation and sonication can be used to burst cells or shake them off of the ECM. Another treatment is electroporation, where cell membranes can be destroyed by electrical pulses (an extension of the electroporation method has been used in conjunction with whole-organ liver perfusion). Other methods, such as temperature treatment and pressure gradients, have also been described. However, this must be done carefully, as physical treatment is often likely to damage the ECM. For this reason, physical treatments are becoming less common, and most papers in the last few years have been using physical treatment sparingly, and usually in conjunction with other treatment methods.

Until very recently, "decellularization" referred primarily to the treatment of tissues, small layers of cells that compose part of an organ. Now, much research is being done on whole-organ decellularization. Through novel treatment methods that usually involve convective flow of a decellularizing agent through an organ's vasculature, biological structures of macroscopically large volumes may be decellularized using just one treatment process. This potentially represents a great improvement in fabrication efficiency, with the ultimate objective being the ability to engineer and mass-produce entire organs for patients in need of organ donation and medical transplants.

Most whole-organ decellularization processes use a technique called perfusion to apply the decellularizing agent. A perfusion system involves connecting a small tube to the point where bodily fluid normally enters that organ and then applying a small flow (usually on the order of 1 mL/min) of one or more decellularizing agents throughout the organ's vasculature for a few hours. This treatment slowly and uniformly removes cellular material from the organ, and the low flow rate is relatively gentle on the ECM.

Though perfusion is employed by most treatment processes, the specific decellularizing agent used varies widely, as it does for tissue decellularization. Akhyari et al. compared four different whole-heart perfusion techniques, all using different combinations of agents (primarily the detergents discussed in the previous section). One protocol, using primarily SDS, EDTA, and Triton X-100, was shown to fully decellularize all four heart chambers without causing major changes to the concentration of glycosaminoglycans (GAGs), an ECM component. However, the same authors studied some other ECM components and did not show results that were as satisfactory, as this protocol caused significant loss of laminin and elastin in Western blots. Other whole-organ decellularization methods exist as well, such as convective flow and electroporation.

Overall, whole-organ decellularization has a more widespread potential benefit than tissue decellularization, but it also comes with more difficult challenges. As with tissue processes, avoiding ECM damage while attaining complete decellularization is a major hurdle, but it is not the only challenge. Recellularization, the process of seeding a tissue scaffold with human cells, is a significant difficulty for decellularized whole organs (whereas it is much simpler for smaller tissues), and this topic alone is the subject of many papers and studies. Furthermore, there is little agreement on post-treatment evaluation. Scaffolds must also be sterilized before they can safely be used in vivo, and sterilization methods that avoid damaging the ECM still need to be developed. While progress has been made in recent years, several breakthroughs are needed before artificial whole-organ transplants can become commonplace in human medicine.

The characteristics of a successfully decellularized tissue or organ are generally agreed upon in the field—the material should be (1) acellular, (2) sterile, (3) of the same chemical composition, and (4) of the same mechanical strength as it was prior to treatment. However, there is little-to-no agreement on quantitative standards for measuring whether or not this state has been achieved. Crapo et al. has suggested the following characteristics to define a fully decellularized material:

Less than 50 nanograms of double-stranded DNA per mg ECM (dry weight)
DNA fragment length of less than 200 base pairs
No "visible nuclear material" after DAPI or H&E staining However, this has yet to become a widespread standard outside. Furthermore, this decellularization standard only addresses the first of the four points mentioned above. Relatively little information is currently available about ECM sterilization. Pre- and post-treatment chemical composition and mechanical properties are often compared in papers, and it is known that ideally the pre- and post-treatment properties would be identical. However, there is no standard available to determine how much deviation in these properties is permissible without compromising the safety or functionality of the scaffold. Additionally, testing to determine these thresholds is impossible in humans because of the obvious ethical implications of testing potentially unsafe products in vivo. The issue is further complicated by potential (and generally unknown or minimally investigated) differences between different tissues and organs and between different mammalian tissue and organ sources analyzed under various protocols.

It is well known that incomplete decellularization of an ECM scaffold prior to implantation will trigger an adverse immune response in the host. In the body, cellular injuries trigger the release of damage-assessing molecular patterns, or DAMPs. These DAMPs trigger the immune system, causing a systemic inflammatory response syndrome, or SIRS. Using cellular and decellularized samples of small intestinal submucosa, Keane et al. showed that the occurrence of this inflammatory response is dependent on macrophage phenotype. For macrophages, the M1 phenotype is destructive and signals the inflammatory SIRS response, while M2 macrophages are constructive and release signals that promote repair, healing, and growth. M1 macrophages are drawn to damaged cells, thus leading to the SIRS response in incompletely decellularized scaffolds.

Their studies and others have shown that ECM scaffolds that are incompletely decellularized cause this same effect in implanted scaffolds. For example, in a comparison between cellular and acellular dermal matrix implantation in the abdominals of vervet monkeys, Xu et al. showed that the acellular implants did not trigger significant immune response, while implants containing cellular material clearly showed the clear presence of inflammation and corresponding cytokine markers. These results elucidate a link between immune response and cellular material, since the acellular dermal matrix triggered no inflammation or cytokine, while the cellular matrix triggered considerable immune response. It also shows that residual cellular material is a long-term problem, since many of the test animals showed increased inflammation with time prior to euthanizing after 90 days.

Some limited clinical testing has been done with skin grafts (skin being among the easiest tissues to decellularize), and it has been shown that decellularized ECM is a potentially favorable option. Burch, et al. studied decellularized cryopreserved allografts (DCAs) of heart valves and compared them with standard allografts. The DCAs were 79% freed from reintervention in the testing, while standard methods were only 63% successful. Here, "reintervention" refers to the necessity for patients to undergo another surgical procedure to repair or replace the allograft; the primary reason for this to occur is immune response triggered by the allograft. The decellularized valves caused no immune response and also were reported to have lower peak valve gradients, though this figure was not statistically significant. Rice et al. compared two ECM products, Surgisis and Alloderm, to Vicryl woven mesh, and found the acellular products to have an increased capacity for neovascularization, as well as better collagen deposition and organization.

As mentioned in the previous section, complete sterilization is also a critical factor in creating viable ECM scaffolds. As reported by Crapo et al., current sterilization methods include specimen treatment with gamma irradiation, electron beams, or ethylene oxide. None of these methods are particularly desirable for ECM sterilization, as $\gamma$-ray and electron beam treatment often cause physical damage to the ECM (thus undermining the decellularization portion of the treatment), and ethylene oxide is only an effective sterilant at temperatures greater than the melting point of collagen.

There is one publication on using supercritical $CO_2$ in decellularization: Sawada et al.: "Cell removal with supercritical carbon dioxide for acellular artificial tissue." *J Chem Technol Biotechnol* 2008, 83(6):943-949, which shows the use of supercritical carbon dioxide containing an ethanol entrainer to decellularize porcine aortas. Sawada et al. reported 100% removal of DNA and 80-90% removal of phospholipids at relatively mild pressures and temperatures. Supercritical carbon dioxide is unique in that it has strong penetrating power into tissues and reverts to the gas phase so that it does not remain in the tissue after treatment. Still, problems with tissue dehydration and residual phospholipids were reported. The dehydration seen by Sawada et al. caused the decellularized matrix to become brittle and lose mechanical strength, making it unsuitable for tissue engineering applications. Sawada et al. concluded that the cause was extraction of water by supercritical $CO_2$. They also determined that an effective post-treatment rehydration step was not possible. Prolonged soaking in aqueous solution only restored the matrix to 90% of its original mass, likely because of slight structural variations that prevented the complete re-absorption of the lost water. Unfortunately, no follow-up studies have been reported.

Recently, Qiu et al. proposed using supercritical carbon dioxide as a sterilization technique for ECM: Qiu et al., "Inactivation of Bacterial Spores and Viruses in Biological Material Using Supercritical Carbon Dioxide With Sterilant." *J Biomed Mater Res Part B* 2009, 91B(2):572-578. Small pieces of decellularized porcine dermal ECM were sterilized using supercritical $CO_2$ with a peracetic acid entrainer. In 27 minutes of treatment time, the authors obtained 6 log reduction of bacillus atrophaeus, a bacterial spore that has traditionally been analyzed for sterilization effectiveness because of the high degree of difficulty in destroying it. They also treated samples for viruses, including encephalomyocarditis (EMC) virus, and attained complete removal in 15 minutes of treatment, which was more effective than two hours of treatment in peracetic acid alone. Additionally, the change in tissue weight percent caused by treatment was less than 2% different from the control, showing a relatively mild impact of treatment.

Supercritical $CO_2$ seems to have considerable potential for ECM sterilization, but more research needs to be performed beyond the report of Qiu et al. In particular, it would be important to attempt supercritical $CO_2$ sterilization on decellularized whole organs, or at least on larger or three-dimensional ECM scaffolds, given that Qiu et al. sterilized only very thin samples of ECM that were only a few square centimeters in area. Furthermore, it may be beneficial to investigate a supercritical $CO_2$ treatment method that combines decellularization and sterilization.

In summary, the field of tissue engineering and decellularization is a promising method for producing acellular tissues and organs that can be used for grafts and implants while avoiding many of the biocompatibility risks presented by synthetic biomaterials. A wide variety of protocols for decellularization of tissues and organs exist, but the field needs considerable improvement before utilizing these techniques for human medical use can become feasible. As has been discussed at length throughout this review, the first and most important challenge is the necessity for treatment methods that do not damage the ECM. Stronger decellularization methods using combinations of chemical, biological, and physical treatments have been developed in recent years, but with this added strength have also come an inability to maintain the chemical and material properties of pre-treatment ECM.

Another significant challenge caused by the nature and diversity of the field is that it can be extremely challenging to compare different decellularization procedures. There are many different decellularizing agents, treatment times, tissue types, and animal sources, and treatment procedures that make it very difficult to analyze the efficacy of one technique compared to another. One method to address this may be to perform more optimization experiments, similar to the ones performed by Akhyari et al. that compared four different decellularization protocols on rat hearts. Analogous experiments using deliberate factorial design in experiments may be beneficial in uncovering treatment methods for each animal and tissue type that are optimal or at least more effective. To aid in these comparisons, a widespread standard that addresses decellularization, sterilization, chemical composition, and mechanical strength would be greatly beneficial.

Another roadblock to advancing decellularization is the necessity of post-treatment processing. This includes recellularization processes in whole-organ decellularization, as well as sterilization processes and thorough quality assurance testing, which will be surely required for any product intended for use in humans. As mentioned earlier in the report, a tissue or organ to be used in a graft or implant must be fully acellular and sterile, and must also be mechanically and chemically similar to the native tissue or organ. This presents many opportunities for contamination or damaging of the ECM, and because of this, treatment methods at all stages will need to be considerably refined in the future.

SUMMARY

Objects and advantages of the invention will be set forth in part in the following description, or may be obvious from the description, or may be learned through practice of the invention.

Decellularization methods are generally provided for tissue.

In one embodiment, the method comprises: exposing a tissue to a water-saturated, supercritical $CO_2$. The method can further comprise, prior to exposing the tissue to the water-saturated, supercritical $CO_2$, saturating a stream of supercritical $CO_2$. The tissue can be exposed to the water-saturated, supercritical $CO_2$ at a treatment temperature of about 35° C. to about 40° C. (e.g., about 37° C.). In one embodiment, the water-saturated, supercritical $CO_2$ is completely saturated with water at the treatment temperature. The tissue can be exposed to the water-saturated, supercritical $CO_2$ at a constant flow rate, such as less than 3 mL/min (e.g., about 0.5 mL/min to about 2.5 mL/min).

In another embodiment, the decellularization method can include: exposing a tissue to a water-saturated, liquid $CO_2$. The method can further comprise, prior to exposing the tissue to the water-saturated, liquid $CO_2$, saturating a stream of liquid $CO_2$. Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DEFINITIONS

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Methods and apparatus are generally provided for an effective $scCO_2$-based decellularization method that overcomes certain limitations discussed above. In particular, the presently disclosed methods provide a major step in developing an effective $scCO_2$-based decellularization method by preventing the tissue dehydration that occurred in the $scCO_2$ decellularization experiments of Sawada et al. Because of the high water content in mammalian tissues (e.g., greater than 80% in a porcine aorta) maintenance of the natural hydration state of the tissue is important to fabricating a suitable TE scaffold.

In the presently disclosed methods, the extraction of water is inhibited from occurring at all. In particular, a simple presaturation method is generally provided by using water-saturated $scCO_2$. The presaturated $scCO_2$ is then contacted with the tissue, but water is not substantially extracted from the tissue. That is, the presaturated $scCO_2$ cannot dissolve any additional water due to the amount of water already within the presaturated $scCO_2$ flow stream, since the amount of water presaturated can be close to or at the saturation limit of the $scCO_2$. In particular embodiments, the flow rate can be relatively low, such as less than about 3 mL/min (e.g., about 0.5 mL/min to about 2.5 mL/min).

Supercritical fluids, like gases, have little or no surface tension, low viscosity, and high diffusivity, but they also have liquid-like densities. This combination of properties allows supercritical fluids to penetrate through surfaces easily without damaging them. Upon depressurization, the supercritical fluids outgases leave no residue in the tissue. In particular, supercritical CO2 is especially useful in biomedical applications. It is inexpensive, readily available, chemically inert, and nontoxic. It has mild critical conditions of 31.1° C. and 7.38 MPa, making it able to treat biological materials at body temperature (37° C.) without reaching excessive pressures. Supercritical CO2 has already been shown to have applications in pasteurization, extraction, and sterilization.

The ability of supercritical $CO_2$ to dissolve small molecules, such as water, is well known. In physical chemistry, saturation is the point at which a solution of a substance can dissolve no more of that substance and additional amounts of it will appear as a separate phase. This point of maximum concentration (i.e., the saturation point) depends on the temperature and pressure of the solution, as well as the chemical nature of the substances involved. With respect to $scCO_2$, the saturation point of water at 50° C. and 2000 psi (which is about 138 bar or 103,430 torr), the equilibrium solubility of water in $CO_2$ is about 0.0084 mole fraction. At 37° C., the equilibrium solubility of water in $CO_2$ would be a little lower, probably around 0.005 mole fraction.

As such, the presently disclosed decellularization methods prevent tissue dehydration and removes all nuclear material from the tissue using liquid carbon dioxide ($lCO_2$) or supercritical carbon dioxide ($scCO_2$), while maintaining the tissue's mechanical integrity during the treatment process. Supercritical $CO_2$ has the unique potential for accomplishing both decellularization and sterilization, which means that one comprehensive protocol may be possible.

EXAMPLES

Here, the construction of an apparatus that can presaturate $scCO_2$ with water is described to determine the range of flow rates where equilibrium-level presaturation can be attained and to compare the amount of water extraction caused by presaturated and dry $CO_2$.

1. Apparatus Development and Validation

First, a presaturation apparatus was developed to determine whether the proposed system could be used to effectively saturate $scCO_2$ with water. The objective of using the apparatus was to ensure that the $scCO_2$ was really being humidified and saturated during the mixing process, and that the flow rate used in Sawada's experiments (1 mL/min) was slow enough for presaturation to be maintained in a dynamic flow system. Confirming these findings was critical before proceeding to subsequent tests.

Figure 1:
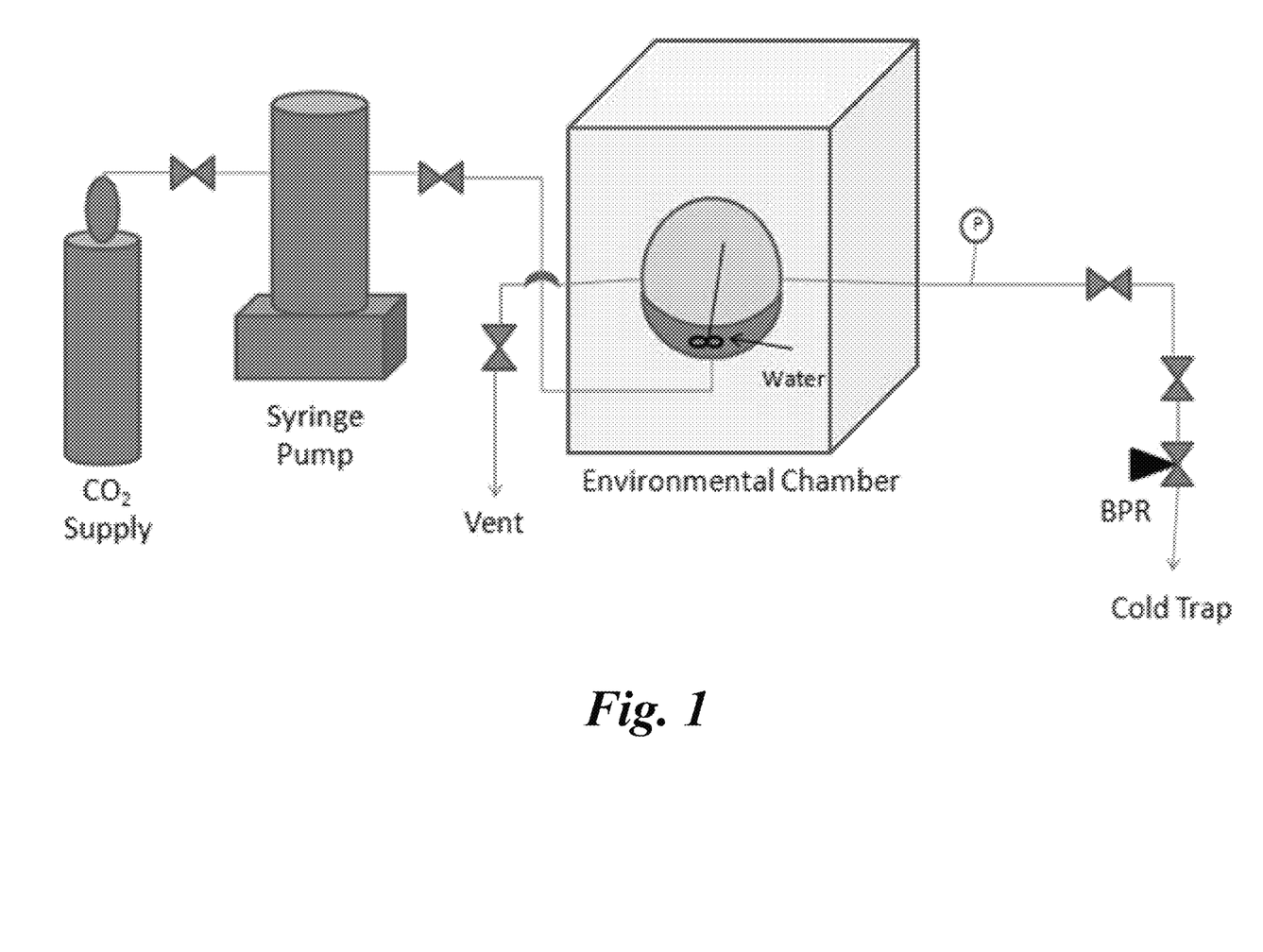
FIG. 1 shows a schematic of presaturation apparatus according to one particular embodiment.
Figure 2:
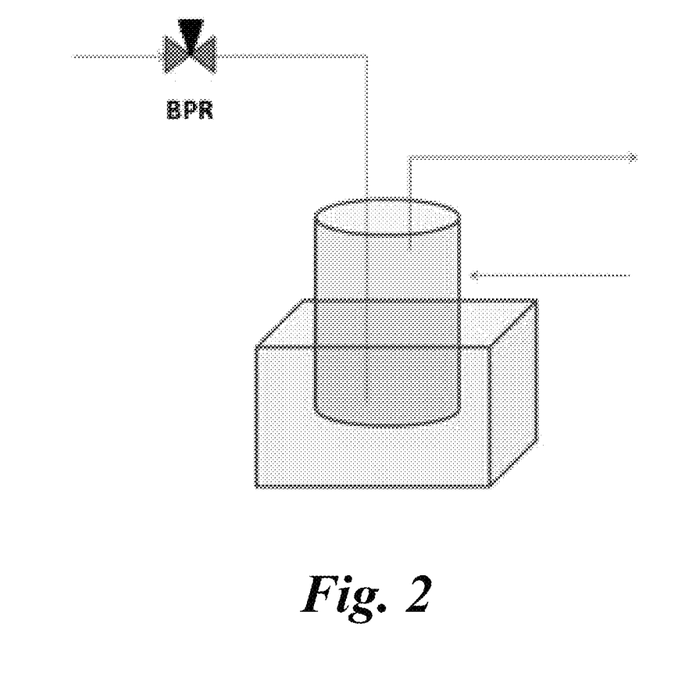
FIG. 2 shows a schematic of a cold trap utilized according to the examples.

The presaturation apparatus is shown in FIG. 1. Liquid carbon dioxide (bone-dry grade with siphon tube, 99.8% purity, Airgas National Welders, Charlotte, N.C.) was compressed to 2000 psi in a chilled syringe pump (500 HP Series, ISCO Inc, Lincoln, Nebr.), and slowly bubbled into a 25 mL stainless steel view cell (Waters Corp, Milford, Mass.) containing 10 mL of deionized (DI) water. The view cell was agitated using a stirrer plate and magnetic stirring bar, all of which were enclosed in an environmental chamber (LU-113 model, ESPEC Corp, Osaka, Japan), which maintained a constant temperature of 50° C. After waiting 15 minutes for thorough mixing, the humidified $scCO_2$ was then flowed at various flow rates into a cold trap (see FIG. 2), which was maintained at −10° C. using a rock salt/ice water bath. The flow rate of the $scCO_2$ was controlled using a back-pressure regulator (TESCOM, Elk River, Minn.). The mass of the trap was measured before and after each experiment using an analytical mass balance (Mettler Toldeo, Columbus, Ohio) to determine the amount of water dissolved in the $scCO_2$ at each flow rate.

The experiments were done at varying $CO_2$ flow rates (1, 2.5, 5, 10, 15, and 20 mL/min, which can also be stated, respectively, as 0.994, 2.49, 4.97, 9.94, 14.9, and 19.9 g/min, since the density of $CO_2$ at these conditions is 0.994 g/mL) but using the same total volume of $CO_2$ (200 mL) each time to allow for fair comparisons between runs. The equilibrium solubility of water in supercritical $CO_2$ at 50° C. and 2000 psi ($\rho$=0.665 g/mL) is 0.00837 mole fraction, so this level must be reached for the flow system to ensure that the $CO_2$ is fully saturated with water and that water will not be extracted from the tissue sample during the decellularization process.

Figure 3:
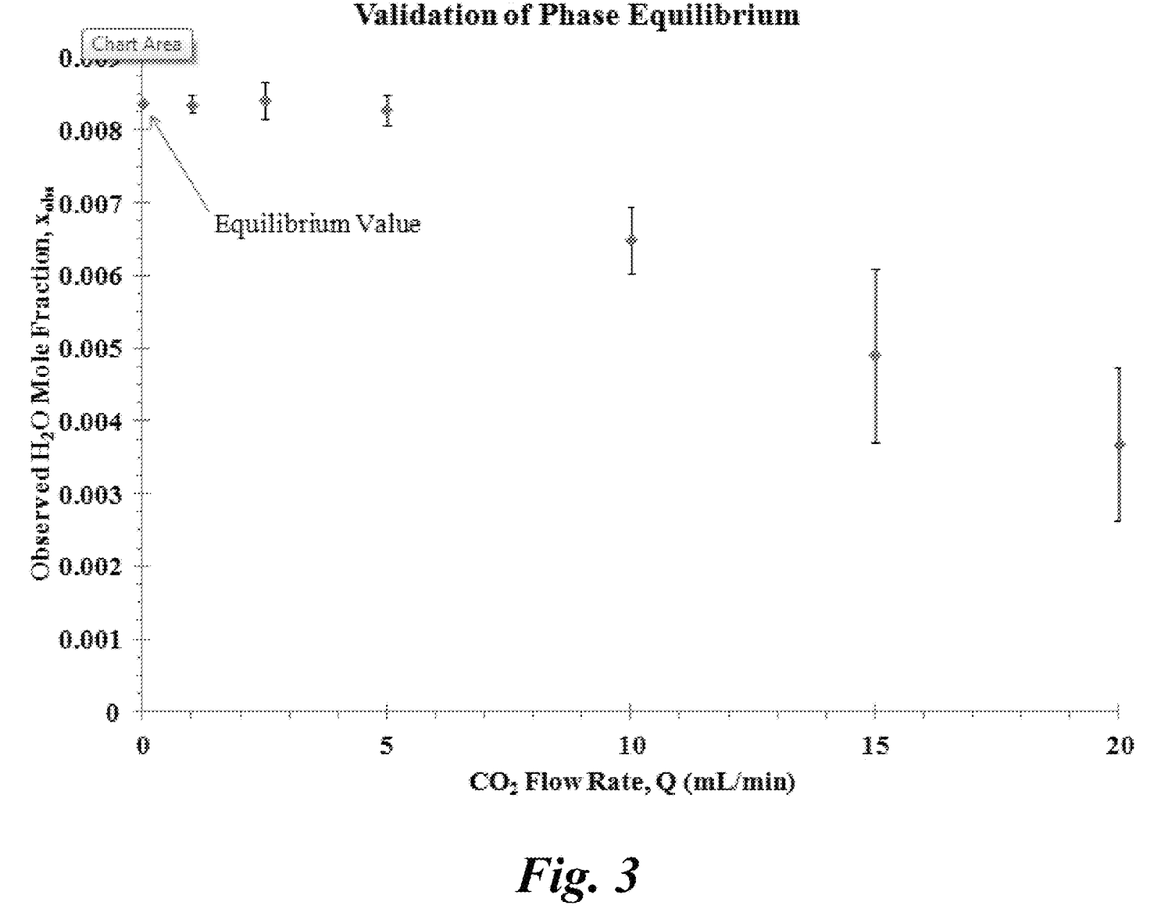
FIG. 3 shows the presaturation test results of the Examples.

For each flow rate, an "observed mole fraction" ($x_{obs}$) was calculated based on the amount of water collected in the cold trap and the amount of $CO_2$ used in the experiment. This $x_{obs}$ value should be equal to the equilibrium value if complete presaturation is achieved. The results obtained are shown in FIG. 3.

The general trend of these results agrees with the hypothesis. At low flow rates, the observed mole fractions are around the equilibrium value, and as the flow rate is increased, the observed mole fraction decreases below this value. This occurs because the flow rate is too fast for adequate mixing to occur in the chamber before it flows into the cold trap.

After confirming that the presaturator does achieve the equilibrium level of water in the $scCO_2$, we moved to performing an experiment that involved contacting an actual test material with humidified $scCO_2$ to determine if it would dehydrate that material compared to dry $scCO_2$. The material chosen for these tests was poly(acrylic acid-co-acrylamide) potassium salt, a powder that swells to form a hydrogel in the presence of water. It has the capacity to absorb up to 200 mL of water per gram of powder. This model hydrogel was chosen for this experiment because, when hydrated, it is essentially composed entirely of water. Therefore, contacting the hydrogel with $scCO_2$ allowed us to measure the extraction of water without having to worry about other variables, since this test avoids the possible complications of testing an animal tissue or other material.

Figure 4:
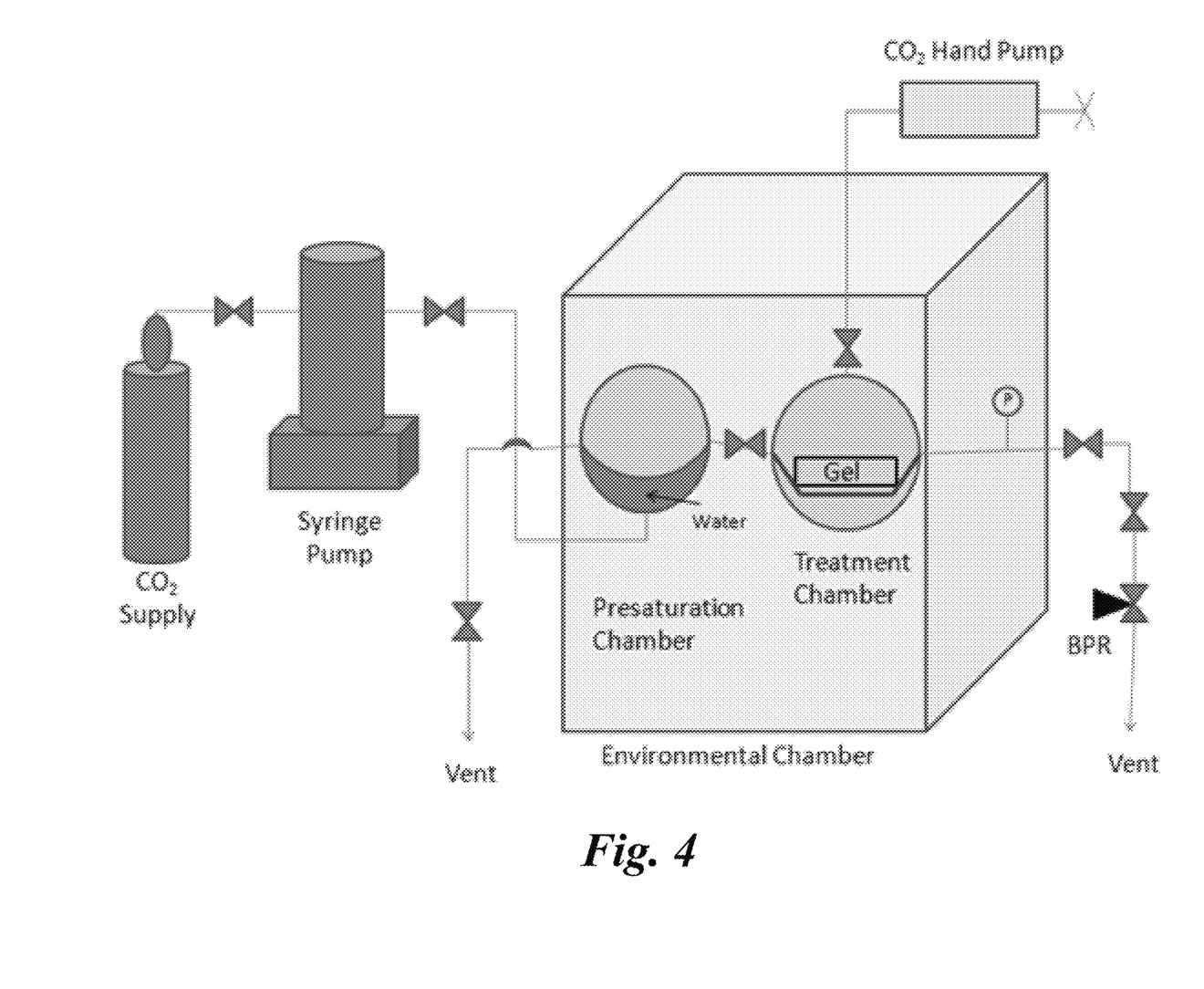
FIG. 4 shows an exemplary hydrogel test apparatus utilized in the Examples.

The tests were performed using the following apparatus, which is similar to the one used in the previous section, but with some changes, described in FIG. 4. The major addition is a second pressure cell, called the treatment chamber. It is a 10 mL view cell that is identical to the 25 mL mixing cell except for its smaller volume. The hydrogel sample, approximately 0.2 g, is fully swelled, blotted onto a nylon filter, and sealed inside the treatment chamber before treatment begins. A hand pump (HiP Pressure Generator 62-6-10, High Pressure Equipment Co., Erie, Pa/) is attached to the treatment chamber and used to maintain a slow, controlled depressurization of 50 psi/min after treatment. Finally, the cold trap is removed, and the $CO_2$ is simply vented.

Four sets of experiments were run: two control groups, where no water was loaded into the presaturation chamber, and two experimental groups, where the presaturator was utilized. All experiments were run at 2000 psi (13.79 MPa) and two different temperatures: 37° C. ($\rho$=0.769 g/mL at the given pressure) and 50° C. ($\rho$=0.665 g/mL). Each set consisted of four separate trials. For each trial, the mass of hydrogel used was approximately 0.2 g. Variation in hydrogel mass was accounted for by varying the treatment time slightly based on the mass of each sample; a treatment ratio of 30 minutes per 0.1 g of gel was used. This and other conditions used (including temperature, pressure, and depressurization rate) were chosen to be very similar to the conditions used by Sawada et al. to allow for easier comparison with their results.

The data obtained are given in the tables below:

TABLE 1

Treatment of Hydrogels with Supercritical $CO_2$ at 37° C.

| Presaturated? | Start Mass (g) | End Mass (g) | % Water Retained |
|---|---|---|---|
| No | 0.202 | 0.125 | 61.7 |
| No | 0.199 | 0.096 | 48.2 |
| No | 0.193 | 0.072 | 37.4 |
| No | 0.198 | 0.116 | 58.9 |
| Dry Average: | | | 51.5% ± 17.6% |
| Yes | 0.193 | 0.191 | 99.4 |
| Yes | 0.207 | 0.206 | 99.2 |
| Yes | 0.199 | 0.199 | 99.7 |
| Yes | 0.204 | 0.201 | 98.2 |
| Presaturated Average: | | | 99.1% ± 1.0% |

TABLE 2

Treatment of Hydrogels with Supercritical $CO_2$ at 50° C.

| Presaturated? | Start Mass (g) | End Mass (g) | % Water Retained |
|---|---|---|---|
| No | 0.2031 | 0.0842 | 41.5% |
| No | 0.2016 | 0.1061 | 52.7% |
| No | 0.1952 | 0.1264 | 64.8% |
| No | 0.1919 | 0.0489 | 25.5% |
| Dry Average: | | | 46.1% ± 26.6% |
| Yes | 0.2079 | 0.2075 | 99.8% |
| Yes | 0.2077 | 0.2072 | 99.8% |
| Yes | 0.2108 | 0.2082 | 98.8% |
| Yes | 0.2032 | 0.1990 | 98.0% |
| Presaturated Average: | | | 99.1% ± 1.4% |

Figure 5:
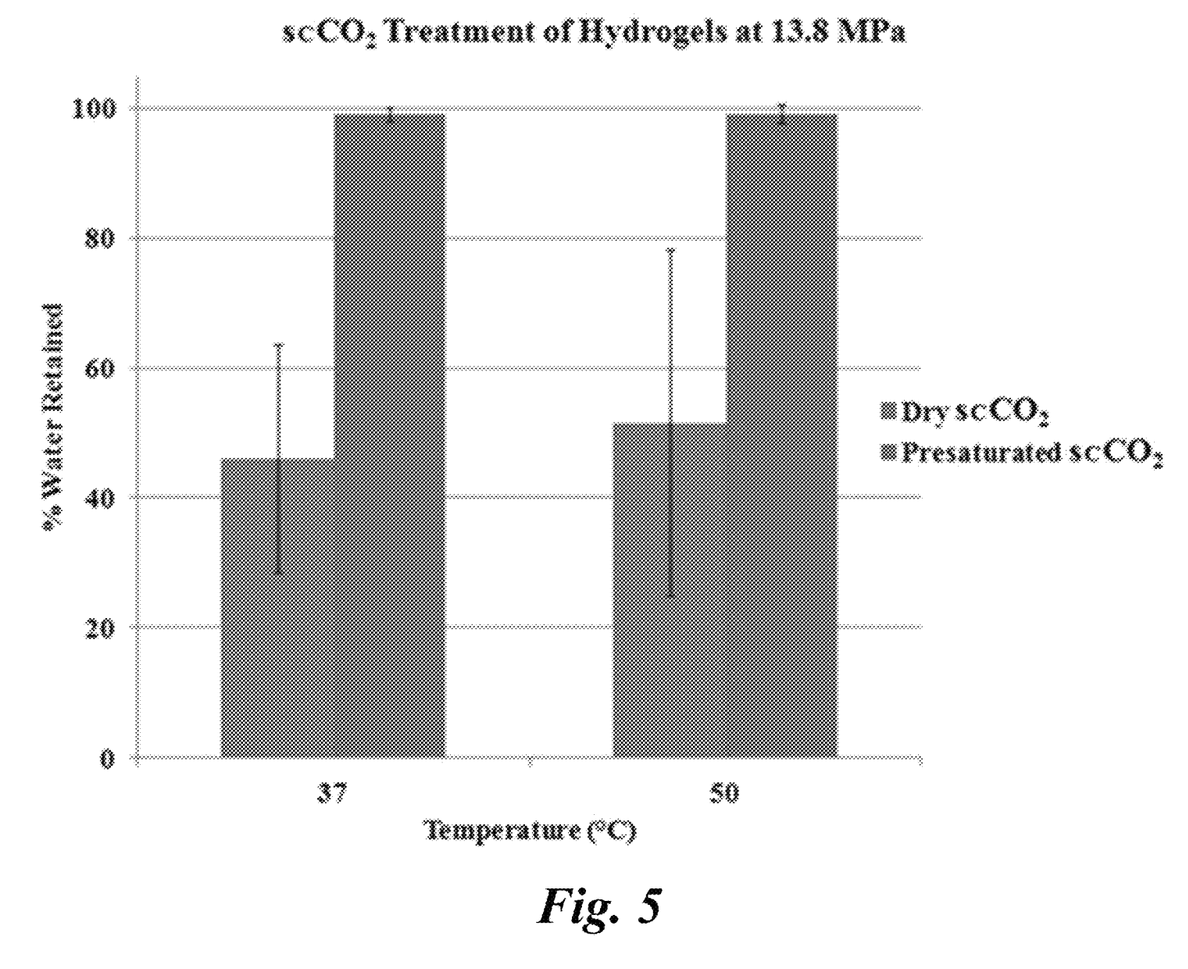
FIG. 5 shows the comparison of the dry $scCO_2$ and presaturated $scCO_2$ hydrogel results at 37° C. and 50° C. according to the Examples.

Statistical analysis was done for the 37° C. data series and the 50° C. data series, with very similar results found for both temperatures. At 37° C., the average water loss was 48.45%±17.64% for the control group and 0.87%±1.05% for the presaturated group. This difference is statistically significant using a Student's t-test with p<0.05. Similar results were obtained at 50° C., with an average water loss of 53.92%±26.58% for the control and 0.93%±1.42% for the presaturated group. This difference was also statistically significant for p<0.05. These results are shown in FIG. 5.

Though the hydrogel results were promising, it was still necessary to perform experiments using actual tissues that could potentially be decellularized to determine the true viability of the presaturation method. Porcine aorta has been chosen to test since it was the tissue studied by Sawada et al., and there is currently a need for tissue-engineered heart valves and blood vessels.

Porcine heart was obtained from a local slaughterhouse, and the aorta was isolated and surrounding fatty tissue was removed. The aortic tissue was cut into thin rectangles (approx. 3 cm×2 cm) and stored in phosphate buffered solution (PBS) at 4° C. for up to 48 hours until use. Each specimen was dried for 15 minutes under a light vacuum using filter paper and a Buchner funnel to remove free saline prior to weighing and treatment. Drying in a vacuum oven (37° C., 15 in Hg vacuum) was used as a negative control; changes in mass were recorded at 1, 2, 3, 6, and 24 hr. For $CO2$ treatments, a tissue section was loaded into the treatment chamber. The same experiments performed in section 3.2 were done with the porcine aorta tissue in place of the hydrogel (see FIG. 4). Tests were performed using dry (positive control) and presaturated (experimental) supercritical CO2 at 2000 psi (13.79 MPa) and 37° C. (p=0.769 g/mL) and with a scCO2 flow rate of 1 mL/min and depressurization rate of 50 psi/min (0.345 MPa/min). Treatment time was determined by using a treatment ratio of 60 min per 0.25 g tissue.

Figure 6:
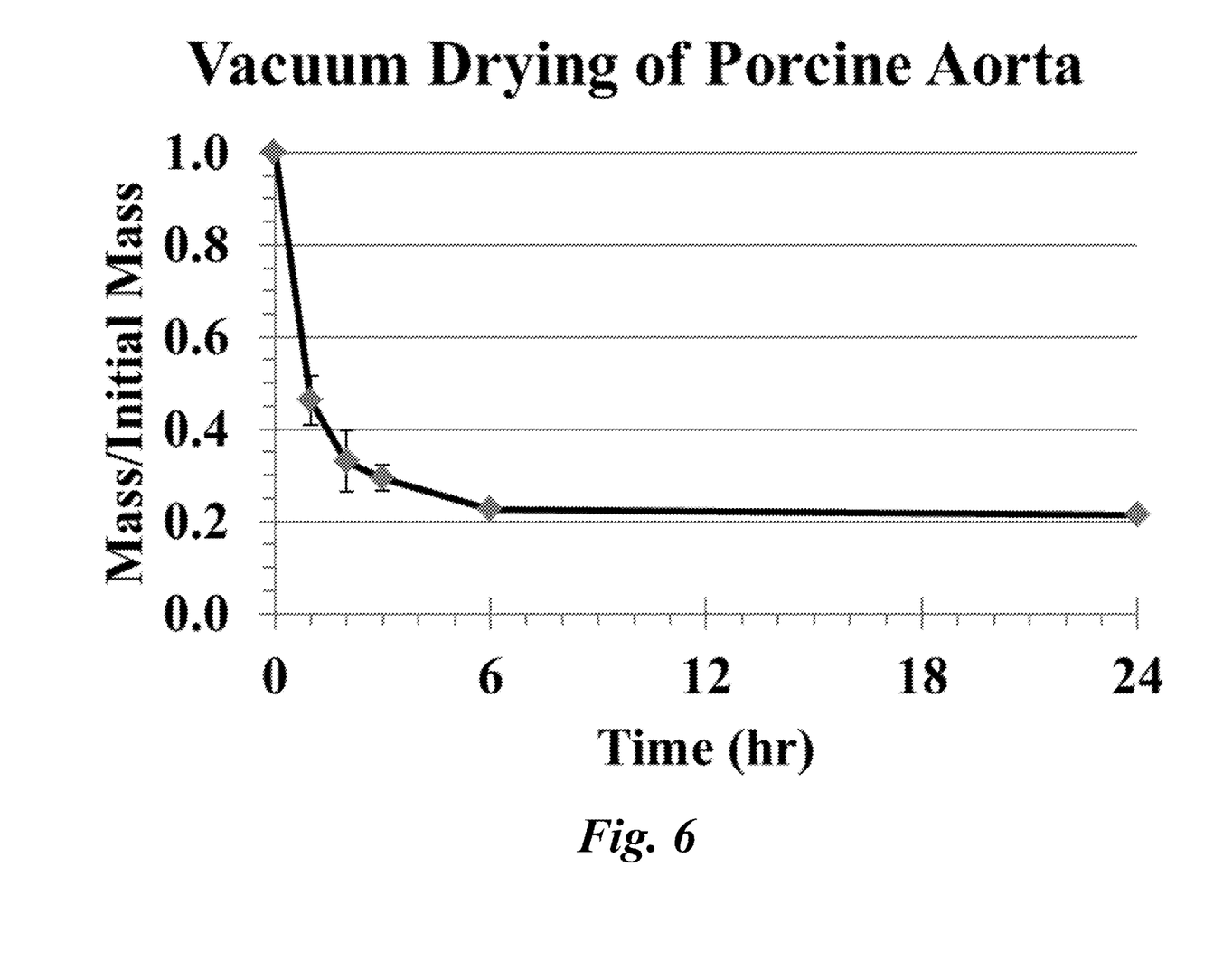
FIG. 6 shows the Porcine Aorta Drying Curve, 0-24 hours, according to the Examples.
Figure 7:
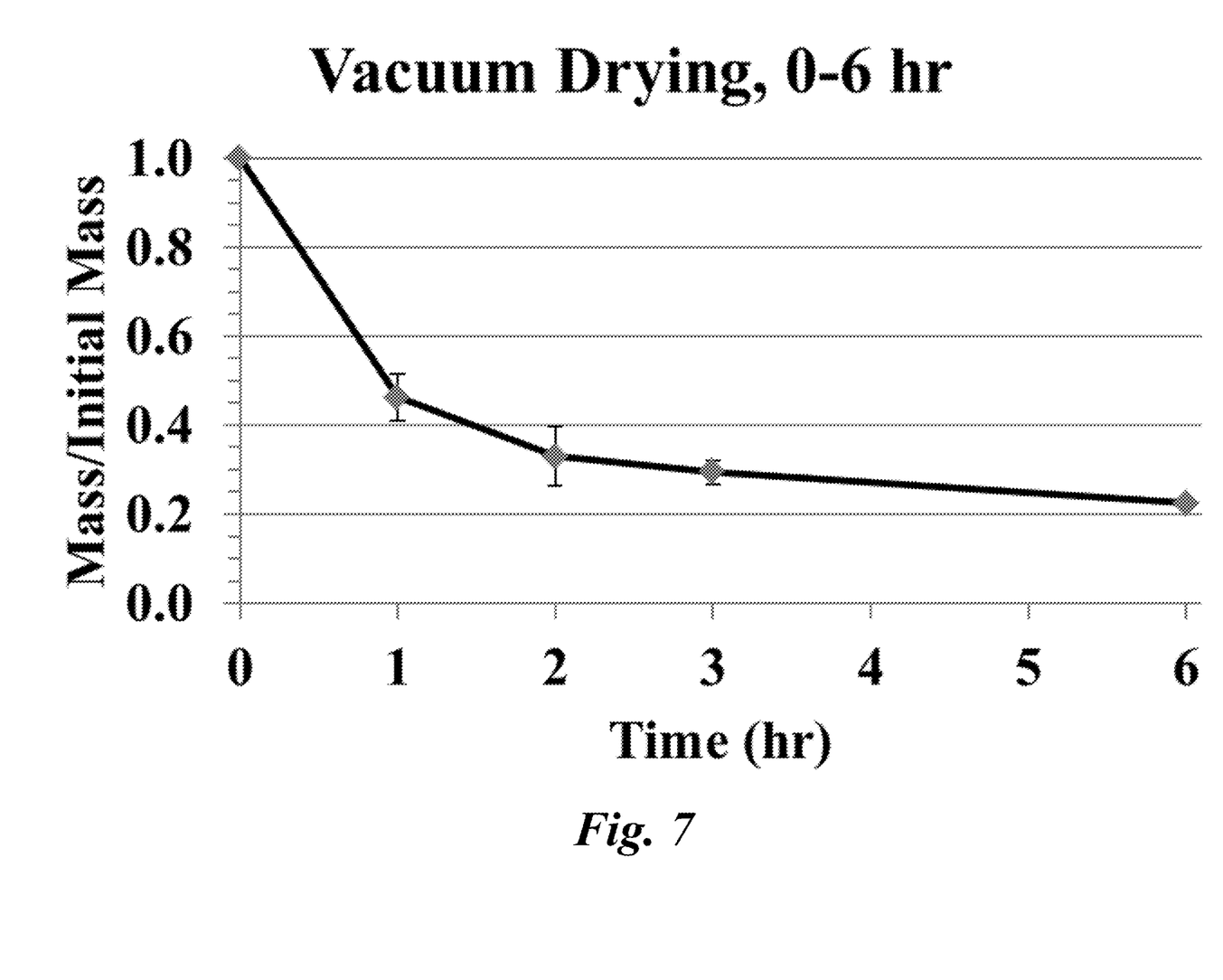
FIG. 7 shows the results of Vacuum Drying of Porcine Aorta, 0-6 hours, according to the Examples.

After vacuum drying the tissue samples, a drying curve was generated for porcine aorta tissue (n=6), as shown in FIG. 6. The change in mass from 6 to 24 hours was found to be relatively insignificant, and therefore only data up to 6 hours is used in other figures. FIG. 7 shows FIG. 6 from 0-6 hours.

Dimensionless mass is plotted on the y-axis to create a uniform drying curve for all samples tested. Vacuum drying of the native tissue removed over half of the initial mass in the first hour, with a continually more gradual decline in mass over the next five hours until reaching about 20% of the initial mass. This final mass makes sense, since the water content of porcine aorta is known to be approximately 80%.

Results for positive control (n=4) and experimental (n=5) supercritical $CO_2$ runs are given in Table 3, below.

TABLE 3

Treatment of Porcine Aorta with Supercritical $CO_2$ at 37° C.

| Presaturated? | Native Mass (g) | End Mass (g) | % Mass Retained |
| --- | --- | --- | --- |
| No | 0.2534 | 0.1967 | 77.6 |
| No | 0.2205 | 0.1793 | 81.3 |
| No | 0.2425 | 0.1819 | 75.0 |
| No | 0.2068 | 0.1664 | 80.5 |
| Dry Average: | | | 78.6% ± 4.6% |
| Yes | 0.1811 | 0.1776 | 98.1 |
| Yes | 0.2148 | 0.2049 | 95.4 |
| Yes | 0.2569 | 0.2518 | 98.0 |
| Yes | 0.2466 | 0.241.1 | 97.8 |
| Yes | 0.2777 | 0.2696 | 97.1 |
| Presaturated Average: | | | 97.3% ± 1.4% |

Figure 8:
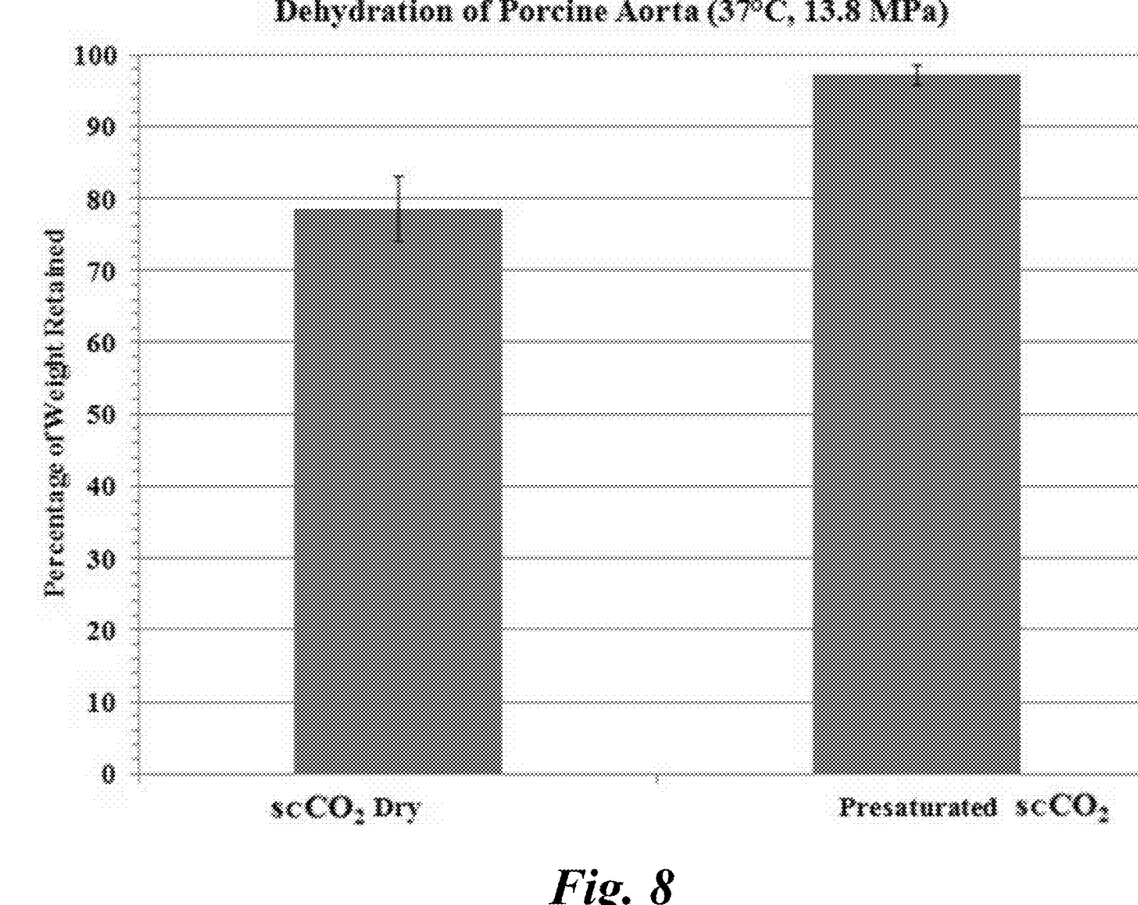
FIG. 8 shows the results of the tissue dehydration comparison of the dry $scCO_2$ and presaturated $scCO_2$ results at 37° C. of the Porcine Aorta according to the Examples.

The average losses in weight are 21.4%±4.6% for dry $CO_2$ and 2.7%±1.4% for presaturated $CO_2$. This difference is statistically significant for p<0.05, as shown in FIG. 8. It can be seen that using presaturated $CO_2$ considerably reduces the amount of mass lost during treatment. However, there is still some mass loss using presaturated $CO_2$, which gives rise to the possibility that a small amount of volatile substances other than water exist in the tissue, which needs to be investigated going forward.

Figure 9:
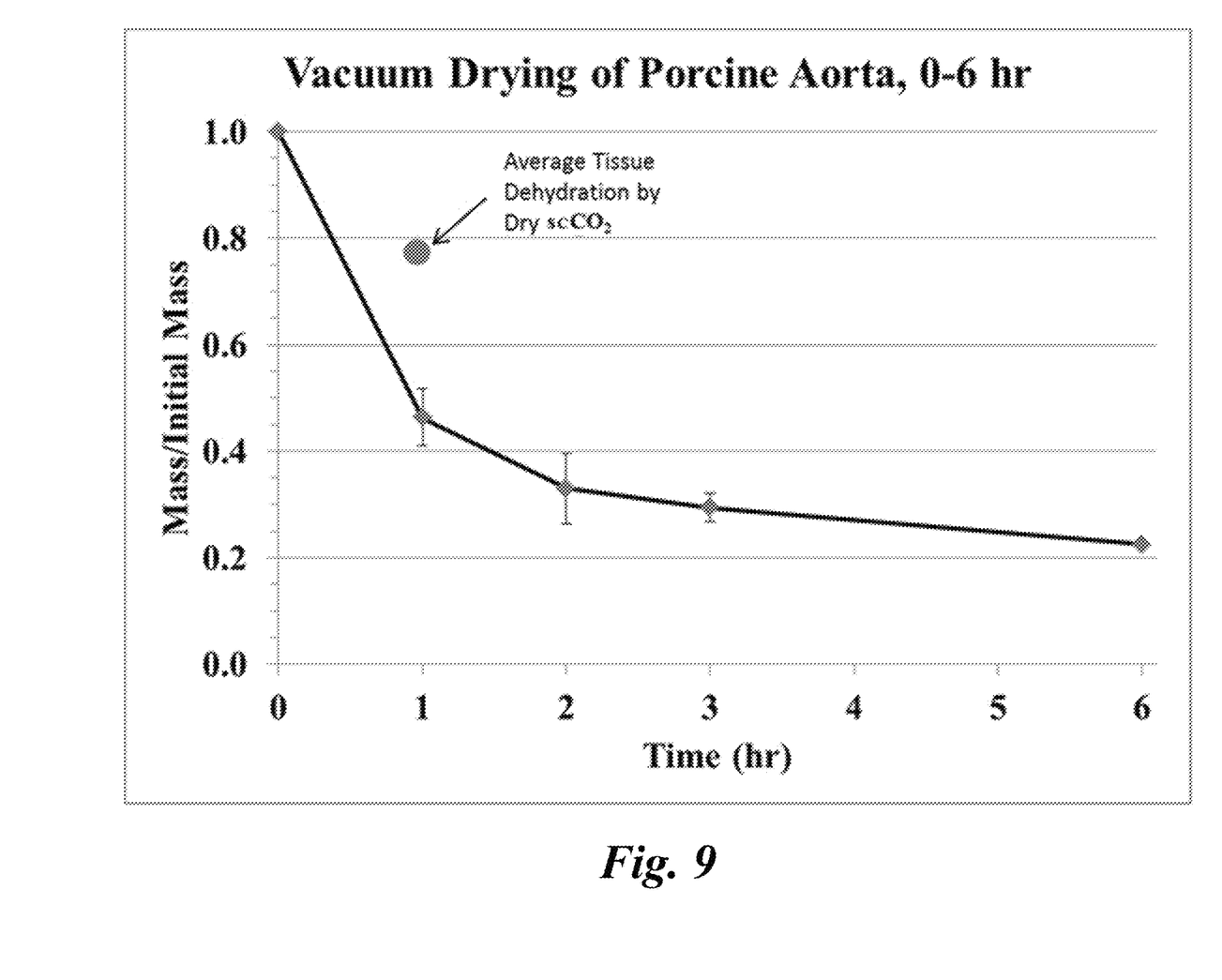
FIG. 9 shows the vacuum drying curve of the Porcine Aorta, compared to $CO_2$, according to the Examples.

Presaturated scCO$_2$ treatment was found to generally not cause extensive water removal. FIG. 9 shows where dry $CO_2$ treatment lies on the tissue drying curve.

A thermodynamic check can also be used to show that this comparison is reasonable. The solubility of water in supercritical $CO_2$ is 0.00837 mole fraction. This value can be used to determine the maximum "extractable water" (EW) based on the moles of $CO_2$ used in the treatment (which varies for each sample based on the treatment ratio). A ratio of actual EW to maximum EW can then be determined, as shown below:

TABLE 4

Thermodynamic Check for Extractable Water

| Dry Sample # | $CO_2$ (mL) | $CO_2$ (mol) | Max EW (g) | Act EW (g) | EW Ratio |
| --- | --- | --- | --- | --- | --- |
| 1 | 60.816 | 1.083 | 0.163 | 0.0567 | 0.348 |
| 2 | 52.920 | 0.942 | 0.142 | 0.0412 | 0.290 |
| 3 | 58.200 | 1.036 | 0.156 | 0.0606 | 0.388 |
| 4 | 49.632 | 0.883 | 0.133 | 0.0404 | 0.304 |

The average ratio of actual to maximum EW is 33.05%, or about one-third. This value is reasonable because the conditions in the treatment chamber are not ideal for maximum extraction.

The Cold Trap Experiments had the following sample calculations:

$$\text{Conditions } T = 50° \text{ C.}, P = 2000 \text{ psi} \rightarrow \rho_{CO2} = 0.665 \text{ g/mL};$$

$$\rho_{H2O} = 0.944 \text{ g/mL}$$

$$V_{CO2} = 200 \text{ mL}, x_{obs,eq} = 0.00837$$

$$\text{Moles CO}_2: n_{CO_2} = 200 \text{ mL} * 0.665 \frac{\text{g}}{\text{mL}} * \frac{1 \text{ mol}}{44 \text{ g}} = 3.028 \text{ mol}$$

$$\text{Moles H}_2\text{O}: n_{H_2O}(\text{from } expt) * \frac{18 \text{ g}}{\text{mol}} * \frac{1 \text{ mL}}{0.994 \text{ g}}$$

$$\text{Observed Mole Fraction: } x_{obs} = \frac{n_{H_2O}}{n_{CO_2}}$$

Overall, the results from this section are very promising. The cold trap experiments show that the presaturation method used can effectively saturate scCO$_2$ with water. The hydrogel experiments show that presaturating scCO$_2$ with water prevents the humidified $CO_2$ from extracting much, if any, water from the substance it contacts. It also shows that presaturation makes a significant difference in preventing this from happening, as the control tests with dry $CO_2$ showed the same water extraction reported by Sawada et. al.

The cold trap tests show that, even in a dynamic system, continuous presaturation can be achieved at low flow rates. The values of observed mole fraction at 1 mL/min and 2.5 mL/min were actually slightly greater than the known solubility of water in scCO2 at equilibrium. This likely occurred because of a light film that forms on the outside of the trap from being in the ice bath and is hard to completely remove prior to weighing the trap, thus increasing the value of the mass measurement just slightly. Regardless of the possible error caused by this, these results clearly show a trend of decreasing xobs as flow rate increases, which was expected based on our theoretical understanding of the process.

The hydrogel experiments, in particular, are strong evidence that the presaturator works as intended. The positive controls show an expected dehydration of the hydrogels over time, caused by extraction of water by the dry $CO_2$, resulting in about a 50% weight loss. The amount of water lost is slightly higher at 50° C., likely because the solubility of water in $CO_2$ increases with temperature, which would cause more water to be extracted at 50° C. than at 37° C. On the other hand, the experimental group shows less than a one percent average weight loss at both temperatures, showing that the humidified $CO_2$ extracts little or no water from the hydrogels. Analogous results were obtained when porcine aorta tissue was treated in place of the hydrogel.

A novel method for treating tissues or other materials with presaturated supercritical $CO_2$ has been presented, and its functionality has been verified by three different sets of experiments. From these results, we conclude that this method could potentially be useful for the decellularization of tissues, and that attempting decellularization is warranted based on these results.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A decellularization method for tissue, the method comprising:
    passing a stream of supercritical $CO_2$ through water retained in a first chamber at a flow rate of less than 3 mL/min and thereby forming a stream of water-saturated, supercritical $CO_2$ that is completely saturated with water;
    feeding the stream of water-saturated, supercritical $CO_2$ that is completely saturated with water into a treatment chamber, the treatment chamber containing a tissue, such that the tissue is exposed to the water-saturated, supercritical $CO_2$ that is completely saturated with water; wherein the exposure causes decellularization of the tissue.

2. The decellularization method as in claim 1, wherein the tissue is exposed to the water-saturated, supercritical $CO_2$ that is completely saturated with water at a treatment temperature of about 35° C. to about 40° C.

3. The decellularization method as in claim 2, wherein the tissue is exposed to the water-saturated, supercritical $CO_2$ that is completely saturated with water at a treatment temperature of about 37° C.

4. The decellularization method as in claim 1, wherein the tissue is exposed to the water-saturated, supercritical $CO_2$ at a constant flow rate.

5. The decellularization method as in claim 4, wherein the flow rate is about 0.5 mL/min to about 2.5 mL/min.

6. The decellularization method as in claim 1, wherein the water-saturated, supercritical $CO_2$ that is completely saturated with water has a water content of about 0.004 mole fraction to about 0.009 mole fraction.

7. The decellularization method as in claim 6, wherein the water-saturated, supercritical $CO_2$ has a water content of about 0.005 mole fraction to about 0.0084 mole fraction.

8. The decellularization method as in claim 1, wherein the tissue is exposed to the water-saturated, supercritical $CO_2$ that is completely saturated with water at a treatment pressure of 2000 psi.

9. The decellularization method as in claim 1, wherein the tissue is exposed to the water-saturated, supercritical $CO_2$ that is completely saturated with water for a treatment time of 30 to 60 minutes per 0.25 to 0.1 gram of tissue.

10. The decellularization method as in claim 1, further comprising following the decellularization, depressurizing the treatment chamber.

11. The decellularization method as in claim 10, wherein the treatment chamber is depressurized at a depressurization rate of 50 psi/min.

12. The decellularization method as in claim 1, wherein following decellularization, the weight of the tissue is from 95.4% to 98.1% of the weight of the tissue prior to decellularization.

13. The decellularization method as in claim 1, wherein the tissue exhibits less than a one percent average weight loss upon the decellularization.

* * * * *